(12) United States Patent
Steward et al.

(10) Patent No.: US 8,609,086 B2
(45) Date of Patent: Dec. 17, 2013

(54) **PREPARATION CREATED FROM AN IN VITRO CULTURE OF DEDIFFERENTIATED, NON-ELICITED CELLS OF THE *ARGANIA* TREE, USE THEREOF FOR TREATING SKIN AGEING, INFLAMMATION AND SCARRING, AND PRODUCTION THEREOF**

(75) Inventors: Nicolas Steward, Pins-Justaret (FR); Anne Mandeau, Toulouse (FR); Nathalie Castex-Rizzi, Colomiers (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 0 days.

(21) Appl. No.: 13/638,029

(22) PCT Filed: Mar. 30, 2011

(86) PCT No.: PCT/EP2011/054965
§ 371 (c)(1),
(2), (4) Date: Sep. 28, 2012

(87) PCT Pub. No.: WO2011/121051
PCT Pub. Date: Oct. 6, 2011

(65) Prior Publication Data
US 2013/0017178 A1    Jan. 17, 2013

(30) Foreign Application Priority Data
Mar. 31, 2010 (FR) .................................. 10 01327

(51) Int. Cl.
*A01N 63/00* (2006.01)
*A01N 65/00* (2009.01)
*A61K 36/00* (2006.01)
*C12N 5/00* (2006.01)

(52) U.S. Cl.
USPC .......................... 424/93.7; 424/725; 435/410

(58) Field of Classification Search
None
See application file for complete search history.

(56) References Cited

U.S. PATENT DOCUMENTS

| | | | |
|---|---|---|---|
| 6,906,106 B2 * | 6/2005 | Chevalier | 514/690 |
| 2004/0042996 A1 | 3/2004 | Pauly et al. | |
| 2004/0047832 A1 | 3/2004 | Pauly et al. | |
| 2005/0265953 A1 | 12/2005 | Ennamany et al. | |
| 2006/0083794 A1 | 4/2006 | Henry et al. | |

FOREIGN PATENT DOCUMENTS

| | | |
|---|---|---|
| EP | 1 213 024 A1 | 6/2002 |
| EP | 1 213 025 A1 | 6/2002 |
| EP | 1 430 900 A1 | 6/2004 |
| FR | 2 553 788 A1 | 4/1985 |
| FR | 2 724 663 A1 | 3/1996 |
| FR | 2 756 163 A1 | 5/1998 |
| FR | 2 756 183 A1 | 5/1998 |
| FR | 2795637 * | 1/2001 |
| FR | 2 847 476 A1 | 5/2004 |
| WO | WO 03/077880 * | 9/2003 |
| WO | WO 03/077880 A1 | 9/2003 |
| WO | WO 03/077881 A2 | 9/2003 |
| WO | WO03/077880 * | 9/2003 |

OTHER PUBLICATIONS

Popov et al. "[44] Antioxidative Homeostasis: Characterization by Means of Chemiluminescent Technique", Methods in Enzymology, vol. 300, 1999, pp. 437-456.
International Search Report, issued in PCT/EP2011/054965, dated Mar. 30, 2012.
George et al., "Micropropagation:Uses and Methods", Plant Propagation by Tissue Culture 3rd Edition, 2000, pp. 29-64.
George et al., "Plant Tissue Culture Procedure—Background", Plant Propagation by Tissue Culture 3rd Edition, 2000, pp. 1-28.
Murashige et al., "A Revised Medium for Rapid Growth and Bio Assays with Tobacco Tissue Cultures", Physiologia Plantarum, vol. 15, 1962, pp. 473-496.
Nagase et al., "Matrix Metalloproteinases", The Journal of Biological Chemistry, vol. 274, No. 31, 1999, pp. 21491-21494.
Neumann et al., "Characterization of Mca-Lys-Pro-Leu-Gly-Leu-Dpa-Ala-Arg-NH2, a Fluorogenic Substrate with Increased Specificity Constants for Collagenases and Tumor Necrosis Factor Converting Enzyme", Analytical Biochemistry, 328, 2004, pp. 166-173.
Popov et al. "[44] Antioxidative Homeostasis: Characterization by Means of Chmiluminescent Technique", Methods in Enzymology, vol. 300, 1999, pp. 437-456.
Van Der Vliet et al., "Effect of Oxidative Stress on Receptors and Signal Transmission", Chem-Biol. Interactions, 85, 1992, pp. 95-116.
Zhai et al., "Determination of the Antioxidative Capacity of an Antioxidant Complex and Idebenone: An In Vitro Rapid and Sensitive Method", Journal of Cosmetic Dermatology, vol. 7, 2008, pp. 96-100.

* cited by examiner

*Primary Examiner* — Jennifer McDonald
*Assistant Examiner* — Qing Xu
(74) *Attorney, Agent, or Firm* — Birch, Stewart, Kolasch & Birch, LLP

(57) ABSTRACT

The invention relates to a preparation created from an in vitro culture of dedifferentiated, non-elicited cells of the Argania tree.

5 Claims, 3 Drawing Sheets

PREPARATION CREATED FROM AN IN VITRO CULTURE OF DEDIFFERENTIATED, NON-ELICITED CELLS OF THE *ARGANIA* TREE, USE THEREOF FOR TREATING SKIN AGEING, INFLAMMATION AND SCARRING, AND PRODUCTION THEREOF

The purpose of this invention is a preparation derived from an in vitro culture of dedifferentiated non-elicited argan cells, a cosmetic or dermatological composition comprising said preparation and its uses for the treatment of skin aging, inflammation and healing.

Argan is a tree that belongs to the botanic Sapotacea family and its scientific name is *Argania spinosa* (L.) Scelles.

Its habit is similar to the olive tree; it has a short and twisted trunk. The wood is very hard and dense. The branches are very thorny and they have small, lanceolate, alternating, short (about 2 cm long) and narrow leaves that are often grouped in clusters. The leaves are evergreen, but they become dead and fall off whenever there is a severe drought. The flowers are hermaphrodite and pentameric. They are grouped in glomerules, and open in May and June. They are greenish-yellow.

The Argan tree can produce fruit starting from the age of 5 years. The fruit is a yellow, oval sessile berry, about 4 to 5 cm long. It is composed of pulp surrounding a nut containing 2 to 3 flat seeds stuck together, each enclosing an oil-rich almond.

The Argan is endemic to Morocco and is located mainly in south-west Morocco between Essaouira and Agadir. The Argan forest covers about 830 000 ha.

Moroccan populations firstly exploited Argan for its particularly hard wood as a fuel supply. The other major traditional use is oil initially extracted manually, but now extracted using a press. The first use of this oil is for food; another important application now is for cosmetics. The pulp and the residual cake derived from this oil production are normally used for animal feed.

Many cosmetology products have been developed from Argan. There have been several invention patents for oil derived from the seeds, for example oil obtained by solvent (Patent Fr 2 553 788), argan oil enriched with unsaponifiable matter (Patent Fr 2 724 663).

Substances other than oil have also been patented, for example peptides derived from seed cake obtained after extraction of oil; combination of oil and peptides from cake for the treatment of problems related to skin aging (Patent Fr 2 756 183). There is also an invention patent for Argan leaves, proteins and saponins from cake=Extracts from leaves (Patent EP 1 213 025), cake proteins (Patent EP 1 213 024), cake saponins (Patent EP 1 430 900). More recently, patent application EP 1 968 536 was deposited disclosing the use of an extract from pulp of argan fruit in anti-aging cosmetics.

Therefore, the composition of the entire argan tree is interesting for dermatological and/or cosmetic use.

Argan is an important resource plant, firstly ecologically because it is an "ecosystem" plant. It is perfectly adapted to areas with droughts, it protects the soil from water and wind erosion and thus prevents the desert from advancing in Morocco. But also economically, because it is a tree with multiple uses.

It is Morocco's leading crop. Thus, the argan forest was protected by a dahir (decree) issued in 1925, stating that the Nation has the superior rights on the argan forest, but that local populations have the usufruct (fruit, dead wood, crops under argan trees). UNESCO recently classified the argan forest as a biosphere reserve.

This is why the use of its wood or leaves for cosmetic use could have serious consequences on this protected plant.

Another means of obtaining molecules of interest from a plant is to prepare totipotent dedifferentiated cell cultures. The use of dedifferentiated plant cells can also avoid some industrialization problems encountered during the development of cosmetic products. With cell culture, the difference in the concentration of substances of interest between different plant batches or harvests disappears. It is also a non-destructive technique relatively easy and inexpensive to set up. Finally, it eliminates the need for extraction since the cells are in a culture medium and the active compounds are either in the culture medium or in the intra-cellular liquid. Therefore simple grinding makes these compounds available.

Patent application WO03077881 discloses a composition for topic application containing at least one homogenate of dedifferentiated and elicited plant cells in an in vitro culture to synthesize at least one phytoalexin. The plant material is preferably derived from a vine.

Thus, this document discloses the cosmetic application of plant cells that could be dedifferentiated and elicited, elicitation leading to a sufficient quantity of secondary metabolites to enable biological activity in topic use.

Surprisingly and unexpectedly, the Applicant has demonstrated that a preparation derived from an in vitro culture of dedifferentiated but non-elicited argan cells has good cosmetic and/or dermatological activities in the fields of anti-aging, inflammation and healing.

The results obtained show that in the specific case of argan, another application of argan cell cultures (non-elicited cells in this case), is possible within the context mentioned above.

Furthermore, obtaining the preparation as disclosed in this invention can eliminate the need for the elicitation step which is an industrially difficult and expensive step; elicitation leads to a much lower biomass yield due to slowing of cellular growth.

Application WO03077881 mentions various ways of performing this elicitation, for example UV radiation for 3 days; carbon dioxide for 24 hours to 2 days; UV radiation and carbon dioxide for 5 days.

The process performed within the framework of this invention consisting of cell dedifferentiation from plant material derived from argan and then culture of cells in suspension, can quickly result in a fine, abundant, homogeneous and sterile biomass of this plant. Cell culture makes it possible to apply pathways for biosynthesis of this plant directly at cellular scale.

Therefore, this invention is aimed at a preparation derived from an in vitro culture of dedifferentiated non-elicited argan cells, a cosmetic or dermatological composition including said preparation and its uses in cosmetology and/or dermatology, and preferentially for the treatment of skin aging, inflammation and healing.

More generally, in vitro cultures of plant tissues in suspension provide a means of producing active organic compounds derived directly from the primary or secondary metabolism of cells.

Plant cells in suspension are in a dedifferentiation state similar to the state of stem cells for animal cell cultures. Therefore, these plant cells are theoretically capable of producing all metabolites observed in the entire plant. Dedifferentiation causes a genetic or epigenetic disturbance of biosynthesis pathways such that the chemical profiles are quantitatively and qualitatively different between the entire plant and the resulting cell strains. Thus, theoretically, reactional intermediates not observed in the entire plant may appear in cell suspension. This provides a new opportunity so that "dormant" chemical biodiversity can be accessed.

In the current state of the art, in general the elicitations (chemical, physical, biological) of cell culture can stimulate and produce more secondary metabolites. In our process according to the invention, we will show that unlike most cases, and surprisingly, elicitation is not necessary but is detrimental to growth of the biomass and to the required biological activities.

DETAILED DESCRIPTION OF INVENTION

Figure 1:
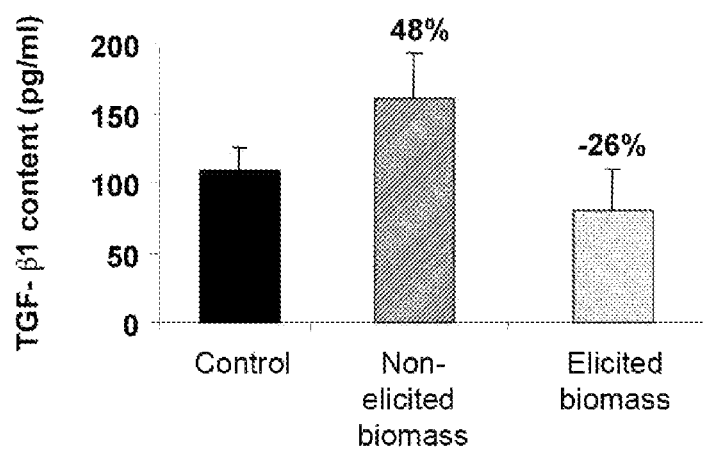
FIG. 1 shows the effects of non-elicited argan biomass prepared according to example 2a and the argan biomass obtained after elicitation on the synthesis of TGF-β1 in human HaCaT keratinocytes.

One of the purposes of this invention relates to the preparation derived from in vitro culture of dedifferentiated non-elicited argan cells.

"Dedifferentiated plant cells" refers to any plant cell without any particular specialization nature, in other words in a physiological state similar to meristematic tissues of the plant in the natural state. These cells are capable of living by themselves and not dependent on other cells.

Dedifferentiated *Argania spinosa* cells are obtained from living plant material picked from the tree or a young shoot, consisting of leaves, leaf stalks, stem, bark, root, fruit, seed, flower and flower organs or the bud, and more particularly from leaves.

The process for obtaining the dedifferentiated cell cultures is obtained in vitro by any method known to those skilled in the art, for example refer to Murashige, T., Skoog, F. 1962. A revised medium for rapid growth and bio assays with tobacco tissue cultures. Physiol. Plant 15: 473-496./Plant Culture Media, Vol-1 Formulations and Uses E.

F. George, D. J. M. Puttock, and H. J. George (1987) Exegetics Ltd. Edington, Westbury, Wilts, BA134QG England.

The preparation according to this invention may be obtained by performing the following steps in sequence:
  a) sterilization of the plant material,
  b) dedifferentiation of the cells,
  c) put into cell suspension with a culture medium without elicitor,
  d) biomass propagation and production culture with a culture medium without elicitor, and obtaining the preparation.

The preparation may be made in an Erlenmeyer flask if the objective is to produce small quantities of biomass or in a bioreactor for larger quantities. For example, the average quantity collected in an Erlenmeyer with 500 ml of cell suspension is 100 g of dried biomass (namely 200 g of biomass/L of cell suspension) while the average dried mass collected in a 10 L bioreactor is 3000 g (300 g/L biomass).

Three main modes are encountered for the plant cell culture in a bioreactor:
  1. discontinuous or batch culture,
  2. recharge/collection or fed-batch culture, and
  3. continuous culture.

a. Plant Material Sterilization Step:

*Argania spinosa* explants and more particularly leaf explants are taken and decontaminated with solutions of sodium or calcium hypochlorite or solutions of mercury chloride at ambient temperature for several minutes. The tissues are rinsed with sterile distilled water and are then washed at least once with sterile distilled water at the end of decontamination.

b. Cell Dedifferentiation Step

The decontaminated explants are placed under a laminar flow hood in contact with a Murashige & Skoog agar nutrient medium to which sucrose and growth factors (or hormones) have been added. These growth hormones will control the cellular machinery of the explants so as to cause cell divisions and to cause cell clusters or dedifferentiated calluses (callogenesis). The calluses obtained will be transferred to a new dedifferentiation nutrient medium every 3 to 4 weeks. Some agar-rich constituents of this medium may be metabolized by the calluses or degraded by the action of air.

In general, a hormonal composition based on auxin (2-4 dichloro-phenoxyacetic acid) and cytokinin (kinetin) was tested successfully to obtain fast and thorough dedifferentiation of tissues in the form of friable calluses (callogenesis) and to facilitate the transfer to a liquid medium. The sterile leaf explants may be deposited on the adaxial face in contact with the agar medium composed of a Murashige and Skoog medium (Murashige, T., Skoog, F. 1962. A revised medium for rapid growth and bio assays with tobacco tissue cultures. Physiol. Plant 15: 473-496) with 30 g/L of sucrose, 8 g/L of agar, with 0.5 mg/L of kinetin and 0.75 mg/L of 2-4 dichloro-phenoxyacetic acid (24D) additives and adjusted to pH 6 before 20 minutes in the autoclave at 121° C. (1 bar). Petri dishes containing explants are left to incubate in darkness at 28° C. The first calluses appear after 2 weeks. The calluses obtained are transferred to a new medium every 3-4 weeks, by dividing the calluses with a scalpel to keep a size of 2 to 3 cm. These transfers continue for 2 to 6 months until friable calluses are obtained.

c. Step to Create Cell Suspension in a Culture Medium without Elicitor.

Cell dedifferentiation for successive transfers of calluses on an agar medium leads to the formation of friable calluses. This drop in the cohesion between the cells is a consequence of the dedifferentiation that may occur at between two and six months depending on the plant. This state is favorable to the transfer to a liquid medium because it guarantees disintegration of the calluses in cell suspension while minimizing the mechanical stresses induced. Thus, a collection of friable calluses is introduced (10-20% by volume) into the liquid nutrient medium prepared using the same formulation as the agar dedifferentiation medium but without a gelling agent.

The friable calluses are thus disintegrated in a liquid medium by the action of a shaking table for 2 to 3 days and the cell suspension obtained is freed of all non-disintegrated callus parts, thus forming a homogeneous cell suspension. This suspension is kept in culture to obtain a sufficiently dense cell population. At this stage, the suspension is (sub-cultured) or diluted in the new nutrient medium and the culture is started in the same way.

An initial cell suspension can be started by depositing about 20 to 40 g of friable calluses in a 500 ml Erlenmeyer containing 200 ml of medium. The friable calluses are thus disintegrated in a liquid medium by the action of a shaking table for 2 to 3 days at 115 rpm in darkness at 29° C. The cell float is then collected using a pipette, leaving the non-disintegrated residual callus clusters apart. The cell float thus forms a homogeneous cell suspension. This suspension is kept in culture to obtain a "sufficiently" dense cell population.

The cell suspension obtained is cultivated for 15 days and is then propagated by dilution to 1:5 in a new medium for the same duration. Adjustments to the composition of the culture medium (nutrients, growth factors, etc.) have been made so as to maximize the biomass productivity. The result is the ARGMS biomass propagation medium (see table 1) optimized for the liquid cell suspension. This medium is a modified version of the Murashige & Skoog medium for callogenesis. This medium is adjusted to pH 6 by the addition of KOH followed by 20 minutes in the autoclave at 121° C. (p=1 bar) or a sterilizing filtration at 0.2 µm.

TABLE 1

ARGMS medium that is a modified version of the Murashige & Skoog (ARGMS) medium used for culture of argan cells in suspension in Erlenmeyer or bioreactor under optimum conditions.
ARGMS medium - optimized for cell growth

| | | |
|---|---|---|
| $NH_4NO_3$ | 2 g/L | Macro elements |
| $KNO_3$ | 2 g/L | |
| $CaCl_2 \cdot 2H_2O$ | 0.33 g/L | |
| $MgSO_4 \cdot 7H_2O$ | 0.25 g/L | |
| $KH_2PO_4$ | 0.3 g/L | |
| KI | 0.83 mg/L | Micro elements |
| $H_3BO_3$ | 6.2 mg/L | |
| $MnSO_4 \cdot 4H_2O$ | 22.3 mg/L | |
| $ZnSO_4 \cdot 1H_2O$ | 6.61 mg/L | |
| $Na_2MoO_4 \cdot 2H_2O$ | 0.25 mg/L | |
| $CuSO_4 \cdot 5H_2O$ | 0.025 mg/L | |
| $CoCl_2 \cdot 6H_2O$ | 0.025 mg/L | |
| $FeSO_4 \cdot 7H_2O$ | 41.7 mg/L | |
| $Na2EDTA \cdot 2H_2O$ | 55.95 mg/L | |
| myo-Inositol | 150 mg/L | Vitamins |
| Nicotinic acid | 0.75 mg/L | |
| Pyridoxin-HCl | 0.75 mg/L | |
| Thiamine-HCl | 0.75 mg/L | |
| Glycine | 2 mg/L | |
| 24D | 0.75 mg/L | Factors (growth hormones) |
| Kinetin | 0.5 mg/L | |
| Sucrose | 35 g/L | Carbonated sources |
| Pyruvate of Na | 3 g/L | | d. Biomass Propagation and Production Culture with a Culture Medium without Elicitor.

After taking several such subcultures, the cell suspension is stabilized when the cell density obtained over the period is constant. Adjustments of the composition of the culture medium (nutrients, growth factors, etc.) are then possible in order to maximize the biomass productivity. In one particular embodiment of the invention, the optimized medium used as the biomass production means is the medium described in table 1.

The cell suspension is filtered to separate it from the extra-cell medium or culture float and the collected biomass is put back into suspension in distilled water and is ground at 0° C. The homogenate obtained is freeze dried or centrifuged so as to clarify it before being freeze dried.

The cell culture under "optimum" condition thus created is stabilized and is kept in an Erlenmeyer (propagation culture) with a 1:5 dilution of the cell suspension every 15 days. This is equivalent to a cell culture of about 60 g/L of fresh biomass inoculated that produces a cell suspension of about 300 g/L after 15 days culture, or inoculated in a bioreactor depending on needs.

The preparation obtained either in Erlenmeyer or in a bioreactor may consist of:

a cell suspension (for the purposes of this invention, "cell suspension" refers to cells (namely biomass) in their culture medium,);

biomass (for the purposes of this invention, "biomass" means a cellular cluster separated from the culture medium, namely the cell suspension after filtration);

ground biomass after putting back (or not putting back) into suspension in distilled water;

a clarified juice or float of biomass ground by centrifuging or by filtration;

a culture float (for the purposes of this invention, a "culture float" is the culture medium in which the cells remained in residence during the culture, or extra-cellular medium).

Regardless of whether the cell suspension, biomass or float of ground biomass is concerned, they may be kept unchanged in frozen form or by the addition of conservation substances such as phenoxy-2-ethanol, benzyl alcohol or any other conservation product appearing in Appendix VI in the EU directive on cosmetic products entitled "List of conservation agents that may be present in cosmetics". They may also be diluted on a cosmetologically acceptable medium such as glycol (propylene glycol, butylene glycol, polyethylene glycols, etc.) in proportions varying from 10 to 60%. The cell suspension or the biomass may also be ground and then conserved as such frozen or by the addition of conservation substances or medium as described above.

Ground or not, the cell suspension, the biomass or biomass float may also be dried by freeze drying or atomization and kept as such or dried on a maltodextrin, lactose or silica type medium or any other cosmetologically acceptable medium.

Finally, the cell suspension may be enriched with useful compounds by affinity chromatography: absorption on resin (Amberlite® XAD®-21a type polystyrene copolymers, etc.) and elution with an appropriate solvent such as ethanol.

Fresh biomass obtained with the process according to this invention represents about 100 to 500 g per liter of suspension, and more preferably between 200 and 350 g per liter of suspension on the optimum collection date (namely about 15 days on average).

The following table expresses the yields obtained (yield in grams of product obtained/L of cell suspension):

| Product | Fresh biomass | | Fresh ground freeze dried biomass | | Fresh ground freeze dried biomass float | |
|---|---|---|---|---|---|---|
| Culture method | Production (preferred) | Productivity (preferred) | Production (preferred) | Productivity (preferred) | Production (preferred) | Productivity (preferred) |
| Erlenmeyer | 150-300 g · $L^{-1}$ in 15 days (200 g · $L^{-1}$ in 15 days) | 10-20 g · $L^{-1}$ · $d^{-1}$ (13 g · $L^{-1}$ · $d^{-1}$) | 7.1-15 g · $L^{-1}$ in 15 days (9.5 g · $L^{-1}$ en 15 days) | 0.4-1 g · $L^{-1}$ · $d^{-1}$ (0.6 g · $L^{-1}$ · $d^{-1}$) | 4.5-9 g · $L^{-1}$ in 15 days (6 g · $L^{-1}$ in 15 days) | 0.3-0.6 g · $L^{-1}$ · $d^{-1}$ (0.4 g · $L^{-1}$ · $d^{-1}$) |
| 10L-Batch bioreactor | 200-500 g · $L^{-1}$ in 15 days | 13-34 g · $L^{-1}$ · $d^{-1}$ (20 g · $L^{-1}$ · $d^{-1}$) | 9.5-24 g · $L^{-1}$ in 15 days | 0.65-1.14 g · $L^{-1}$ · $d^{-1}$ (0.95 g · $L^{-1}$ · $d^{-1}$) | 6-15 g · $L^{-1}$ in 15 days | 0.4-1 g · $L^{-1}$ · $d^{-1}$ (0.6 g · $L^{-1}$ · $d^{-1}$) |

-continued

| Product | Fresh biomass | | Fresh ground freeze dried biomass | | Fresh ground freeze dried biomass float | |
|---|---|---|---|---|---|---|
| Culture method | Production (preferred) | Productivity (preferred) | Production (preferred) | Productivity (preferred) | Production (preferred) | Productivity (preferred) |
| 10L-Fed Batch 80% bioreactor | (300 g · L$^{-1}$ in 15 days) 200-500 g · L$^{-1}$ (300 g · L$^{-1}$ in each 6-day collection) | 32-80 g · L$^{-1}$ · d$^{-1}$ (48 g · L$^{-1}$ · d$^{-1}$) | (14.3 g · L$^{-1}$ en 15 days) 9.5-24 g · L$^{-1}$ (14.3 g · L$^{-1}$ in each 6-day collection) | 1.5-3.85 g · L$^{-1}$ · d$^{-1}$ (2.28 g · L$^{-1}$ · d$^{-1}$) | (9 g · L$^{-1}$ in 15 days) 6-15 g · L$^{-1}$ (9 g · L$^{-1}$ in each 6-day collection) | 0.96-2.4 g · L$^{-1}$ · d$^{-1}$ (1.44 g · L$^{-1}$ · d$^{-1}$) |
| 10L-continuous culture bioreactor $\mu = 0.2$ d$^{-1}$ | 100-500 g · L$^{-1}$ (140 g · L$^{-1}$ continuously) | 20-100 g · L$^{-1}$ · d$^{-1}$ (28 g · L$^{-1}$ · d$^{-1}$) | 4.8-24 g · L$^{-1}$ (6.6 g · L$^{-1}$ continuously) | 1-5 g · L$^{-1}$ · d$^{-1}$ (1.33 g · L$^{-1}$ · d$^{-1}$) | 3-15 g · L$^{-1}$ (4.2 g · L$^{-1}$ continuously) | 0.6-3 g · L$^{-1}$ · d$^{-1}$ (0.84 g · L$^{-1}$ · d$^{-1}$) |

This invention also relates to a cosmetic or dermatological composition comprising a preparation derived from a culture of non-elicited dedifferentiated argan cells as the active constituent, as described above.

Preferably, the quantity of said preparation is between 0.1 and 10% of the total weight of the composition. And even more preferentially, said quantity of extract is between 0.2% and 5%.

The cosmetic composition according to this invention may advantageously be in any galenic form normally used in the cosmetics for a topic or oral application, and preferentially a topic application. For an administration by topic path, the galenic form may be a cream, a gel, an ointment or a spray. The oral formula is chosen from the group comprising tablets, capsules and powders for drinkable suspensions.

The cosmetic composition according to the invention also comprises the usual cosmetically compatible excipients.

The usual excipients compatible with the cosmetic composition may be any excipient among those known to those skilled in the art, so as to obtain a cosmetic composition for a topic application in forms like those described above.

The cosmetic and/or dermatological composition according to the invention may in particular contain additives and formulation aids such as emulsifying, cleaning, foaming type surfactants, etc., complexing agents, thickeners, gelling agents, stabilizers, conservation agents including antimicrobials and antioxidants, conditioners, acidifiers, alkalizing agents, softeners, solvents, coloring agents and fragrances.

The inventors have also shown that preparations derived from dedifferentiated non-elicited argan cells may have the following activities:
- anti-oxidizing, anti-radical activity to limit the oxidation process related to intrinsic and extrinsic aging and the inflammatory process.
- activity on the extra-cellular matrix to improve the mechanical properties of the mature skin (firmness, elasticity, tonicity) through inhibition of metalloproteases degrading collagen.

Finally, this invention relates to a composition disclosed herein for the treatment of skin aging, inflammation and healing.

The following examples are given as non-limitative examples.

Examples for Producing the Preparation According to This Invention

EXAMPLE 1

Fresh Biomass/Process Done in an Erlenmeyer

Argan leaves preferably 3 to 4 months old are sterilized by several baths in sequence: 70% alcohol for 1 minute, 2% sodium hypochlorite for 3 minutes and then rinsed with two successive demineralized water baths lasting 8 minutes and 10 minutes.

Sterilized leaf explants are deposited on an adaxial face in contact with the agar medium composed of a Murashige and Skoog medium (Murashige, T., Skoog, F. 1962. A revised medium for rapid growth and bio assays with tobacco tissue cultures. Physiol. Plant 15: 473-496) with 30 g/L of sucrose, 8 g/L of agar, complemented with 0.5 mg/L of kinetin and 0.75 mg/L of 2-4 dichloro-phenoxyacetic acid (2.4-D) and adjusted to pH 6 before 20 minutes autoclaving at 121° C. (1 bar). The Petri dishes containing explants are left to incubate in darkness at 28° C. and propagated until friable and stabilized calluses are obtained.

The initial cell suspension is created by depositing about 40 g of friable calluses in a 500 ml Erlenmeyer containing 200 ml of autoclaved medium, for which the composition is described in table 1 mentioned above.

The culture is left for one week on a shaking table at 115 RPM in darkness at 29° C. The cell float is then collected with the pipette, leaving residual clusters of calluses. The cell suspension obtained is cultivated for 15 days and is then propagated by 1:5 dilution in the new medium for the same duration.

The suspension is then filtered under a vacuum and the biomass is recovered. The yield of fresh biomass obtained is 168 g/L.

The biomass is kept at −20° C.

EXAMPLE 2

Dry Biomass

EXAMPLE 2a

Dry Biomass/Process Done in Bioreactor in Batch Culture

Four 500 ml cell suspension Erlenmeyers obtained as described in example 1 are put together in an inoculating device and form a 2 L inoculum that is poured sterile into a 10 L bioreactor. This bioreactor is filled with 8 L of optimum medium (see table 1), complemented by 30 mg/L of previously sterilized anti-foam then cooled and kept at 29.5° C. by thermostat-controlled water circulation in a closed circuit in the bioreactor casing.

An oxygen probe is calibrated by saturation and inputs data into a computerized pO2 regulation device in real time. This device keeps the pO2 at 80% by injection of sterile pure oxygen into the aeration system. This bioreactor is also equipped with a CO2 online measurement device at the effluent gases (head space) that at the same time inputs data to a computerized pCO2 regulation device to keep pCO2 at 6%. This is done by injection of sterile atmospheric air into the aeration device mixed with oxygen. The bioreactor is also equipped with a propeller type stirring system rotating at 75 RPM, to stir the cell suspension and prevent it from sedimenting. An automatic device is installed on the output side of the bioreactor, to enable sterile sampling and monitoring of the biomass.

The batch culture is kept under these constant temperature and dissolved gas conditions for 15 to 17 days, to reach a cell density of 280 to 320 g/L of fresh biomass. The bioreactor is emptied after this batch culture is complete, and the biomass is collected by filtration on a filter using a Büchner funnel.

The collected fresh biomass dissolved in the same distilled water volume is ground cold using an "ultrasonic cleaner", and then freeze dried.

EXAMPLE 2b

Dry Biomass/Process Done in Bioreactor in Fed-Batch Culture 10.0.0.1

Four 500 ml cell suspension Erlenmeyers were used as inoculum as described in example 2a. The bioreactor is prepared as indicated in example 2a. Dissolved gas, temperature and stirring regulation systems are prepared as indicated in example 2a.

The initial culture is maintained under these constant temperature and dissolved gas conditions for 15 to 17 days until a cell density of 280 to 320 g/L of fresh biomass is achieved. 80% of the content of the 10 L bioreactor is taken out after this initial culture is completed. 8 L of cell suspension is then collected. The biomass in this suspension is collected by filtration on a filter using a Büchner funnel. 2240 g to 2560 g of fresh biomass is collected. The fresh biomass collected dissolved in the same volume of distilled water is ground when cold using a ultrasonic cleaner and is then freeze dried. 100 to 130 g of freeze dried biomass is obtained.

At the same time as the 80% partial collection is made, 8 L of previously autoclaved and cooled ARGMS medium is poured in the bioreactor then containing 2 L of cell suspension, so as to restore the culture volume to 10 L. The Fed-batch culture is kept under these constant temperature and dissolved gas conditions for 5 to 7 days until a cell density of 280 to 320 g/L of fresh biomass is achieved. This culture is faster (greater productivity) than the initial culture because the biomass is in a sustained physiological cell division state such that pouring of new nutrient medium is characterized by a latency phase of less than 24 hours and an immediate expansion of the biomass. At the end of this Fed-batch culture, 80% of the 10 L bioreactor is removed. 8 L of cell suspension is then collected. The biomass of this suspension is collected by filtration on a filter using a Büchner funnel. The culture is then restarted as before.

EXAMPLE 2c

Dry Biomass/Process Carried Out in Continuous Culture Bioreactor

Four 500 ml cell suspension Erlenmeyers are used as inoculum as described in example 2a. The bioreactor is prepared as indicated in example 2a. The dissolved gas, temperature and stirring regulation devices are prepared as described in example 2a.

The initial culture is kept under these constant temperature and dissolved gas conditions for 10 days, until a cell density of 150 g/L and an instantaneous fresh biomass growth rate of 0.2 $d^{-1}$ are reached. At this stage, 1.2% of the content of the 10 L bioreactor is removed every 1 hour and 20 minutes. These samples are automatically compensated by pouring the same volume of new ARGMS medium into the bioreactor. This method maintains the cells in a constant physiological state and cell density.

100 to 120 ml of cell suspension is then collected. The biomass in this suspension is collected by filtration on a filter using a Büchner funnel. 15 g to 18 g of fresh biomass is collected for each sample. The fresh biomass collected dissolved in the same volume of distilled water is ground cold using a ultrasonic cleaner and then freeze dried. The result obtained is 0.71 to 0.85 g of freeze dried biomass for each drawing off. The culture is thus maintained for at least 60 days. It is theoretically possible to maintain it with no time limit.

The advantage of continuous culture over the previous modes is that there is no need to prepare the bioreactor again requiring cleaning and sterilization, and there is no cell latency phase. Drawing off 1 to 1.5% of the cell suspension automatically followed by compensation with a new medium in the bioreactor causes minimal variations in the composition of the culture medium in progress in the bioreactor. Thus, the cell population does not make any metabolic readjustments for the latency phase responsible for a loss of biomass volume productivity observed in other culture modes.

EXAMPLE 3

Fresh Biomass Float, Said Biomass being Obtained as Described in Example 2a 20 g of fresh ground biomass obtained as described in example 2a is centrifuged at 10000 g for 15 minutes, and the float is collected. It is then freeze dried.

The average yield is 30 mg of freeze dried float per g of fresh biomass.

Examples of Cosmetic Compositions

EXAMPLE 4

H/E Formula

| Component | % |
| --- | --- |
| Fresh biomass (example 1) | 5 |
| Glycerin | 10.0 |
| Na2EDTA | 0.1 |
| Xanthan gum | 0.3 |
| C12-C15 alkyl benzoate | 10.0 |
| Octyl palmitate | 5.0 |
| Conservation agents | qs |
| Stearic alcohol | 2.5 |
| Glycerol monostearate | 2.5 |
| Potassium cetyl phosphate | 1.8 |
| Demineralized water | QSP 100 |

EXAMPLE 5

E/H Formula

| Component | % |
| --- | --- |
| Float (example 3) | 0.5 |
| Glycerin | 4.0 |
| Na2EDTA | 0.1 |
| MgSO$_4$ | 1.0 |
| Xanthan gum | 0.1 |
| C12-C15 alkyl benzoate | 12.5 |
| Isohexadecane | 3.5 |
| Cyclomethicone | 3.0 |
| Conservation agents | qs |
| Polyglycerol and sorbitan esters | 4.0 |
| Myreth-3 myristate | 2.0 |
| Demineralized water | QSP 100 |

EXAMPLE 6

Evaluation of the Anti-Oxidizing Activity Chemiluminescence

This method generates free radicals (superoxide radical $O_2^{o-}$) by a photochemical signal. The intensity of oxidation is 1000 times greater than that obtained under normal conditions. Detection is done by chemiluminescence and is used to evaluate lipo or hydrosoluble anti-oxidizing extracts or molecules. The results are expressed as an equivalent quantity of vitamin C or Trolox (6-Hydroxy-2,5,7,8-tetramethylchroman-2-carboxylic acid). The sensitivity is of the order of one nanomole.

The analysis of the results depends on two criteria, namely the shape of the curve (integration) and the numerical value given by the software in nanomoles. (Igor Popov and Gudrun Lewin. Methods in enzymology [44] vol 300. 437-456; Maibach I Howard and coll. Journal of Cosmetic Dermatology Vol 7(2) 96-100 (2008)).

The results will be expressed in μg of sample necessary to obtain an activity equivalent to the activity detected for 1 μg of standard (=trolox). (ACL Kit).

Results:

The anti-oxidizing activity studied in this test represents the ability to specifically trap superoxide anions by chemiluminescence.

TABLE 2

Evaluation and quantification of the anti-oxidizing power in trolox equivalent.

| Tested sample | ACL μg of sample for 1 μg of Trolox |
| --- | --- |
| Trolox (reference) | 1 |
| Float (example 3) | 171 |
| Coenzyme 10 = Reference anti-oxidizing molecule | 272 |
| Biomass (example 2a) | 278 |

The freeze-dried biomass prepared according to example 2a and the float of ground freeze-dried biomass prepared according to example 3 have a globally equivalent anti-radical trapping activity.

278 μg of freeze dried biomass is necessary to obtain an activity equivalent to the activity detected for 1 μg of trolox: activity equivalent to coenzyme Q10, the reference anti-oxidizing molecule.

171 μg of ground freeze-dried biomass float is necessary to obtain an activity equivalent to the activity detected for 1 μg of trolox.

Free radicals, for which production is increased as a result of external aggressions (cold, pollution, tobacco, UV) are responsible for damage to the skin cell DNA, but also cellular and mitochondrial membrane DNA. These free radicals also play a very important role in the inflammation process. These very reactive metabolites are second messengers of cell oxidation stress signaling and therefore early mediators of inflammation (A. Van Der Vliet and coil, Chem Biol Interaction 85: 95-116 1992).

The anti-radical activity of the preparations described in examples 2a and 3 help to resist intrinsic and extrinsic skin aging and inflammation.

EXAMPLE 7

Evaluation of the Inhibition of the Metalloproteasic Activity on Collagen Forming the Extra-Cellular Matrix The extra-cellular matrix (ECM) is a dynamic structure with a structural and regulating role for tissues. It gives the skin its turgescence and mechanical properties. At the epidermis, it occupies the intercellular space and it provides support for the epidermic structure. It also controls exchanges between epidermis cells and plays a role in cell activity. It is composed of fibers, particularly collagen and fundamental substances (water, salts, glycoproteins, glycosaminoglycanes). Collagens are fibrous proteins, formed from three polypeptidic chains that may be identical or different, connected by covalent hydrogen bonds. Collagens form the essential component of the fibrous network and play a mechanical role providing resistance and elasticity for the skin.

When a cell is senescent, most components of the ECM are degraded by zinc-rich endopeptidase type enzymes called Matrix Metalloproteinases (MMPs) (Hideaki Nagase §and J. Frederick Woessner. J Biol Chem, Vol. 274, Issue 31, 21491-21494, Jul. 30, 1999). They are membranous or secreted. All MMPs have a strong sequence and structure homology but differ in the specificity of the substrate. MMP1 or "interstitial collagenase" predominantly degrades type I collagen (80% of the content in the dermis of normal skin) and also degrades type II VII VIII and X collagens.

On a model of a human recombining enzyme using a specific peptidic substrate Mca-Lys-Pro-Leu-Gly-Leu-DPA-Ala-Arg-NH2, we have analyzed the effect of extracts on direct enzymatic activity by fluorimetric quantification (David Leppertd and colt, Analytical Biochemistry 328 (2004) 166-17).

The activated enzyme is pre-incubated with the different preparations and is then put in the presence of the substrate. The enzyme cleaves the peptide separating the Mca fluorophore (7 methoxycoumarin-4-yl)acetyl) from the quencher Dpa (N-3-(2,4-Dinitrophenyl)-L-2,3 diaminopropionyl). The peptide then emits fluorescence with a wavelength of 405 nm when it is excited at 320 nm. Thus, the enzyme activity of MMP-1 is measured and is proportional to the emitted fluorescence.

With this in tubo test, we are able to detect potential MMP1 activity inhibitors, an enzyme with a crucial role in initiation of the degradation of collagens. We measure percentages of MMP1 activity inhibition.

Calculation of the Percentage of Enzymatic Inhibition Related to the Inhibitor or the Product:

$$\% \text{ inhibition} = 100 \times \frac{\left(\begin{array}{c}\text{Maximum net enzymatic activity / Net}\\\text{enzymatic activity in the presence of inhibitor}\end{array}\right)}{\text{Maximum net enzymatic activity}}$$

Results:

The float prepared according to example 3 significantly inhibits the MMP1 activity and dependent dose from 60 to 500 µg/ml.

TABLE 3

Float of freeze dried ground biomass (prepared according to example 3), results of inhibition of the MMP1 in percent (%).

| Mean inhibition % | Concentration in µg/ml |
|---|---|
| 100 | 500 |
| 58 | 300 |
| 41 | 150 |
| 20 | 60 |

The freeze dried biomass prepared according to example 2a was tested from 60 to 1000 µg/ml. Due to the physico-chemical interference of the biomass as a whole, we were unable to measure the inhibiting activity. However, a very similar extract was tested and showed significant inhibitions from 60 µg/ml to 1000 µg/ml.

The extract prepared according to the example 3 can resist the increased activity of MMPs when senescence occurs and can contribute to maintaining the mechanical role of collagen, thus providing resistance and elasticity to the skin.

EXAMPLE 8

Measuring the Synthesis of TGF-β1 in HaCaT Keratinocytes

TGF-β1 (Transforming Growth Factor-beta 1) belongs to the super-family of TGF-β secreted by different cell types and that play an important role in the control of cell growth and regulation of multiple cell responses and biological processes. The major activities of cytokines in this super family are that they modulate proliferation of most cells, they stimulate the proliferation of fibroblasts and increase the formation of the extra-cellular matrix (Lawrence, 1996). TGF-β1 is also involved in the repair of injuries, healing processes (Cullen et al., 1997) particularly by inducing reorganization of the cell cytoskeleton (actin) and promoting migration of epithelial cells (Boland et al., 1996). The cell population most represented at the skin tissue is the keratinocyte population. It forms an important source of growth factors that might control and influence the behavior of skin cells, namely fibroblasts (Ghahary et al., 2001).

Apparatus and Methods
Production of Non-Elicited Biomass: According to Example 2a
Preparation of Elicited Biomass Murashige & Skoog medium is prepared without growth factors (kinetin and 24D). This medium is adjusted to pH 6 by the addition of KOH followed by 20 minutes autoclaving at 121° C. (p=1 bar). This medium is then inoculated at 1:5 of the volume using a cell suspension derived from a propagation culture. Elicitation conditions are created immediately afterwards by the sterile addition of a concentrated solution of 6-benzylaminopurine (BAP or (N-(phenylmethyl)-7H-purin-6-amine) and elicitor agents (acetylsalicylic acid and methyljasmonate) into the kinetin DMSO. The result is an EMS elicitation medium (see table 4). The elicited culture is then maintained for 15 days on a shaking table in darkness at 115 RPM and at 29° C. The fresh biomass is then collected and dried on a Büchner funnel before being ground and centrifuged, and the float is stabilized by freeze drying.

TABLE 4

EMS medium, namely the Murashige & Skoog modified medium used for the culture under elicited conditions of argan cells in suspension in an Erlenmeyer. EMS medium - elicitation medium

| | | | |
|---|---|---|---|
| $NH_4NO_3$ | 1.650 | g/L | Macro |
| $KNO_3$ | 1.900 | g/L | elements |
| $CaCl_2 \cdot 2H_2O$ | 0.44 | g/L | |
| $MgSO_4 \cdot 7H_2O$ | 0.37 | g/L | |
| $KH_2PO_4$ | 0.17 | g/L | |
| KI | 0.83 | mg/L | Micro |
| $H_3BO_3$ | 6.2 | mg/L | elements |
| $MnSO_4 \cdot 4H_2O$ | 22.3 | mg/L | |
| $ZnSO_4 \cdot 1H_2O$ | 6.62 | mg/L | |
| $Na_2MoO_4 \cdot 2H_2O$ | 0.25 | mg/L | |
| $CuSO_4 \cdot 5H_2O$ | 0.025 | mg/L | |
| $CoCl_2 \cdot 6H_2O$ | 0.025 | mg/L | |
| $FeSO_4 \cdot 7H_2O$ | 27.8 | mg/L | |
| $Na2EDTA \cdot 2H_2O$ | 37.8 | mg/L | |
| myo-Inositol | 100 | mg/L | Vitamins |
| Nicotinic acid | 0.5 | mg/L | |
| Pyridoxine-HCl | 0.5 | mg/L | |
| Thiamine-HCl | 0.5 | mg/L | |
| Glycine | 2 | mg/L | |
| 6-benzylaminopurine (BAP) | 1 | mg/L | Factors (growth |
| Kinetin | 1 | mg/L | hormones) |
| Acetylsalicylic acid | 100 | µM | Eliciting |
| Methyl jasmonate | 100 | µM | agents |
| Sucrose | 35 | g/L | Carbonated |
| Na Pyruvate | 3 | g/L | sources |

HaCaT keratinocytes are treated for 5 h with the different extracts, and the cells are then incubated for 24 h in DMEM at 37° C. TGF-β1 is dosed in the culture floats with an ELISA kit.

The effects of non-elicited argan biomass prepared according to example 2a and the argan biomass obtained after elicitation on the synthesis of TGF-β1 in human HaCaT keratinocytes are shown in the appended FIG. 1. They show that in HaCaT keratinocytes, the non-elicited argan biomass prepared according to example 2a (50 µg/mL) stimulates the synthesis of TGF-131 by 48% while the elicited argan biomass inhibits the synthesis of TGF-β1 by 26%.

EXAMPLE 9

Measurement of the Proliferation and Cell Migration of Human Keratinocytes

EXAMPLE 9. a

Measurement of Cell Proliferation of Human Keratinocytes

Healing of injuries is a complex and dynamic biological process that involves the interaction of many local and systemic factors in the normal repair of tissues. Progress of healing comprises four interdependent phases: hemostasis, inflammation, proliferation and remodeling. Proliferation implies three clearly observable processes, namely granulation, contraction and reepithelialization.

During granulation, proliferation of cells that will be involved in the rest of the repair process is observed, with migration of these cells towards the bed of the injury. These cells include macrophages, fibroblasts and endothelial cells. Macrophages continuously release chemotactic factors and growth factors. Fibroblasts construct the new cell matrix necessary for the growth of cells at the bottom of the injury. This scaffolding facilitates cell migration.

Contraction of the injury is a mechanism for reduction of the size of the injury and fibroblasts play a leading role in this contraction.

Reepithelization consists of regenerating an epidermis that covers an injury to reform an effective barrier against the external environment, capable of being pigmented and restoring its sensorial and immunity functions. Therefore it implies keratinocyte cell migration and proliferation processes, but also differentiation of this neo-epithelium and restoration of a basement membrane reconnecting the dermis and the epidermis. When the migration of basal cells towards the centre of the injury enables the two sides of the injury to join together, a wave of cell mitosis occurs to fill in the spaces left by the migration and to supply cells for the epithelial tissue in three-dimensional regeneration.

Proliferation steps of keratinocyte cells, fibroblasts and endothelial cells may be considered as being one of the functional phenomena confirming the healing activity of an active constituent. An increase in the proliferation of fibroblasts or endothelial cells would participate in healing of the dermis, while an increase in the proliferation of keratinocytes would participate in re-epithelization.

Apparatus and Methods: Cell Proliferation

The technique used measures the incorporation of a nucleotide, 5-bromo-2'-deoxyuridine (BrdU), an analogue of thymidine, into the DNA of cells in phase S.

Keratinocytes, isolated from skin discarded after surgery, are cultivated in a complete KSFM (BPE 25 µg/ml; EGF 1.5 mg/ml). The cells are incubated in the presence of molecules to be evaluated for 48 h at 37° C. in an atmosphere with 5% CO2.

Incorporation of BrdU proportional to the cell proliferation rate is evaluated by a system of anti-BrdU antibodies coupled to peroxidase. The addition of a substrate of peroxidase develops a colored reaction (Biotrak Elisa System). The corresponding absorbance (DO) is measured at 450 nm. Therefore this data is proportional to the cell proliferation rate.

The proliferation percent is then determined using the following formula:

$$\% \text{ proliferation} = \frac{DO \text{ treated}) - DO(t control \text{ min})}{DO(t control max) - DO(t control min)} \times 100$$

Note:
$Control_{min}$=cells incubated with the minimum medium
$Control_{max}$=cells incubated with the complete medium
Thus, $Control_{min}$ corresponds to 0% proliferation, and $Control_{max}$ to 100% proliferation.

Figure 2:
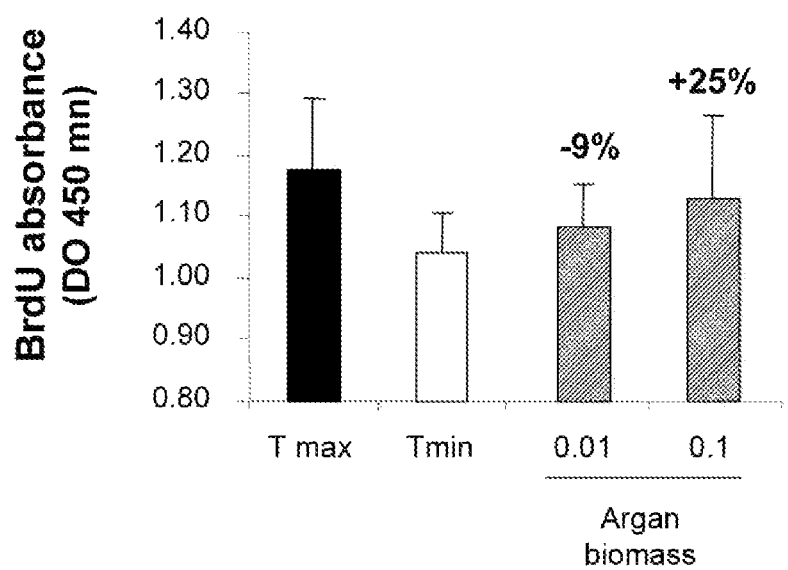
FIG. 2 shows the results on cell proliferation that illustrates the effect of argan biomass prepared according to example 2a on the proliferation of human keratinocytes.

The results on cell proliferation are shown in FIG. 2 that illustrates the effect of argan biomass prepared according to example 2a on the proliferation of human keratinocytes.

They show that the argan biomass prepared according to example 2a at 0.1 µg/mL, stimulates proliferation of human keratinocytes by 25%. No effect is measured when the biomass is tested at 0.01 µg/mL.

EXAMPLE 9.b

Measurement of Cellular Migration of Human Keratinocytes

Apparatus and Methods: Cell Migration of HaCaT Keratinocytes

The protocol used to study the cell migration is based on the use of a 96-well kit. The principle of this test consists of studying the migration of cells towards the centre of the well (96-well plate). To achieve this, a stopper is placed at the centre of each well, so as to create a 2 mm diameter detection zone. The HaCaT cells are then seeded around this stopper. The stoppers are withdrawn once the cells are well bonded to the surface around the stoppers, and the cells can thus migrate to the detection zone. The plates without the stoppers and with active constituents are incubated at 37° C. for 24 hours in DMEM 0% SVF. The quantity of cells located in the zone in which the stopper was located is then analyzed, in order to evaluate the migration of cells. The cells are marked with Hoechst 33342 and a cache is used to view and count only the cells located in this zone. An average of eight wells is made for each condition.

The results are expressed
as a fluorescence intensity (IF-proportional to the quantity of cells that have migrated).
as an activity percent relative to the control 0% SVF:

$$\frac{IF \text{ treated} - IF \text{ 0\% mig}}{IF \text{ tcontrol 0\% SVF} - IF \text{ 0\% mig}} \times 100$$

Note:
IF (0% mig) corresponds to the IF (fluorescence intensity) of wells containing the stoppers and therefore to the background noise.

Figure 3:
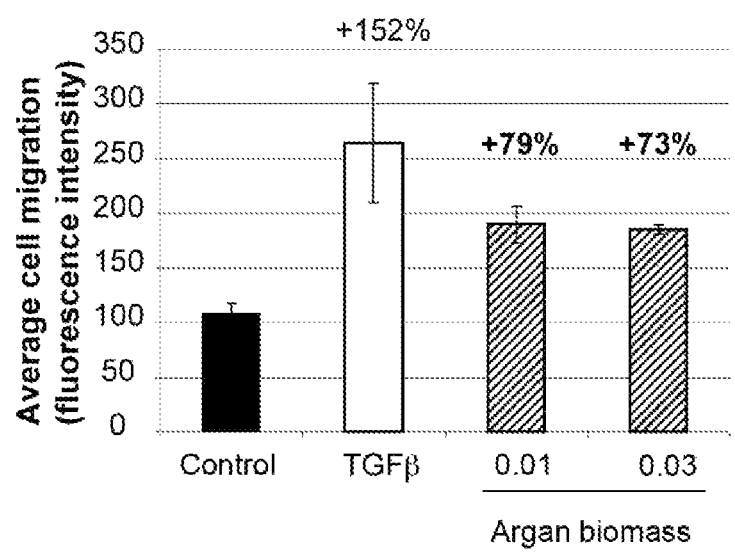
FIG. 3 shows the results of cell migration and illustrates the effect of argan biomass prepared according to example 2a on migration of HaCaT keratinocytes.

FIG. 3 shows the results of cell migration and illustrates the effect of argan biomass prepared according to example 2a on migration of HaCaT keratinocytes.

They show that the argan biomass prepared according to example 2a, at 0.01 or 0.03 µg/mL, stimulates migration of HaCaT keratinocytes by 79% and 73% respectively.

The invention claimed is:
1. A cosmetic or dermatological composition comprising:
a preparation derived from a culture of non-elicited dedifferentiated argan cells as an active constituent, and
a cosmetic or dermatological acceptable excipient,
wherein said preparation is in the form of a culture-medium-free cell suspension, biomass, or ground biomass.
2. The composition according to claim 1, wherein the preparation is between 0.1 and 10% of the total weight of the composition.
3. A method of making the cosmetic or dermatological composition of claim 1 comprising the following sequential steps:
a) sterilizing argan plant material comprising argan cells to generate sterilized argan cells,
b) dedifferentiation of the sterilized argan cells to generate dedifferentiated argan cells,
c) suspending the dedifferentiated argan cells in a culture medium without elicitor, d) propagating the dedifferentiated argan cells in the culture medium without elicitor to generate a population of dedifferentiated non-elicited argan cells, e) harvesting the population of dedifferentiated non-elicited argan cells from the culture medium without elicitor, thereby obtaining a preparation derived from a culture of non-elicited dedifferentiated argan cells, and f) adding a cosmetic or dermatological acceptable excipient to the preparation derived from a culture of non-elicited dedifferentiated argan cells.

4. A method of treating skin aging or skin inflammation, said method comprising applying the composition according to claim 1 to the skin in a person in need thereof.

5. A method of treating skin aging or skin inflammation, said method comprising applying the composition according to claim 2 to the skin in a person in need thereof.

* * * * *